United States Patent [19]

Muth

[11] Patent Number: 5,824,496

[45] Date of Patent: Oct. 20, 1998

[54] CONTROL OF ABERRANT EXPRESSION VECTOR ACCUMULATION DURING FERMENTATION PROCEDURES

[75] Inventor: William L. Muth, Greenwood, Ind.

[73] Assignee: Eli Lilly and Company, Indianapolis, Ind.

[21] Appl. No.: 513,598

[22] Filed: Aug. 10, 1995

Related U.S. Application Data

[63] Continuation of Ser. No. 24,897, Mar. 1, 1993, abandoned, which is a continuation of Ser. No. 371,579, Jun. 26, 1989, abandoned.

[51] Int. Cl.⁶ .............................. C12P 21/02; C12P 19/34; C12N 15/70; C12N 1/21

[52] U.S. Cl. .................... 435/69.1; 435/91.1; 435/172.3; 435/317.1; 435/320.1

[58] Field of Search .............................. 435/69.1, 172.1, 435/172.3, 320.1, 317.1, 91.1; 935/33, 38, 61, 72, 73, 79, 83, 84

[56] References Cited

U.S. PATENT DOCUMENTS 4,529,695   7/1985   Weisblum .............................. 435/69.1

FOREIGN PATENT DOCUMENTS 0101273   8/1983   European Pat. Off. ..
0178764   8/1985   European Pat. Off. ..

OTHER PUBLICATIONS

Mosbach, K. et al. 1983. *Nature* vol. 302 pp. 543—545.
Mott, J.E. et al. 1985. *Proc. Nat. Acad Sci USA* vol. 82 pp. 88–92.
Schein, C.H. 1989. *Bio/Technology* vol. 7 pp. 1141–1149.
Kopetzki, E. et al. 1989. *Mol. Gen. Genet.* vol. 216 pp. 149–155.
Carrier, M.J. et al. 1983. *Trends Biotechnol.* vol. 1 pp. 109–113.
Siegel R. et al. 1985. *Biotechnol. Bioengineer.* vol. 27 pp. 28–33.
Rodriquez, R. et al. 1976. *ICN—UCLA Symp. Mol. Cell. biol* vol. 5 pp. 471–477.
Mott, J.E., et al., 1985. *Proc.Natl.Acad.Sci* USA, vol. 82, pp. 88–92.
Schein, C.H., 1989. *Bio/Technology*, vol. 7, pp. 1141–1149.
Kopetzki, E., et al., 1989. *Mol. Gen. Genet* vol. 216, pp. 149–155.
Carrier, M.J., et al., 1983. *Trends in Biotech.* vol. 1, No. 4, pp. 109.113.
Siegel, R., et al., 1985. *Biotech. and Bioengineer.*, vol. 27, pp. 28–33.
Rodriquez, R. et al. 1976. *ICN—UCLA Symp.Mol.Cell. Biol.* vol. 5, pp. 471–477.
Michel–Briand, et al., 1986. *J. Antimicrob. Chemother.* vol. 18, pp. 667–674.
Trevors, 1986. *FEMS Microbiol. Rev.* vol. 32, pp. 149–157.
Wolfson, et al., 1982. *J.Bacteriol.* vol. 152, pp. 338–344.
Weisser, et al., 1985. *Antimicrob. Agents and Chemother.* vol. 28, pp. 700–702.
Weisser, et al., 1986. *J. Antimicrob. Chemoth.* vol. 18, pp. 575–583.
Caunt, et al., 1988. *J. Biotech.* vol. 8, pp. 173–192.
Pinches, et al., 1985. *Biotech. Letters,* vol. 7, pp. 621–626.
Michel–Briand, et al., 1986. J. Antimicrob. Chemother. 18:667–674.
Trevors. 1986. FEMS Microbiol. Rev. 32:149–157.
Wolfson, et al., 1982, J. Bacteriol. 152:338–344.
Weisser & Wiedmann, 1987, J. Antimicrob. Chemother., 18:575–584.

*Primary Examiner*—Nancy Degen
*Attorney, Agent, or Firm*—Paul J. Gaylo; Paul R. Cantrell; David E. Boone

[57] ABSTRACT

The present invention provides a method for preventing the accumulation of aberrant expression vectors during fermentation processes which rely on the expression of an expression vector coded gene for production of a polypeptide product of interest. Antibiotics are added at approximately the time at which product expression begins.

25 Claims, 10 Drawing Sheets

Figure 6
A Fermentation Process Using Cinoxacin to Control Aberrant Expression Vector Replication During Production of EK-bGH

Construction of Plasmid pL32

Construction of Plasmid pL32

Construction of Plasmid pL32

Restriction Site and Function Map of Plasmid pNM789

Construction of Plasmid pL110

Construction of Plasmid pL110

Construction of Plasmid pL110

Restriction Site and Function Map
pCZR125

A Fermentation Process Using Cinoxacin to Control Aberrant Expression Vector Replication During Production of EK-bGH

CONTROL OF ABERRANT EXPRESSION VECTOR ACCUMULATION DURING FERMENTATION PROCEDURES

This application is a continuation of application Ser. No. 08/024,897, filed on Mar. 1, 1993, now abandoned, which is a continuation of application Ser. No. 07/371,579, filed on Jun. 26, 1989, now abandoned.

FIELD OF THE INVENTION

The present invention relates generally to the field of biotechnology, in that it discloses the use of antibiotics to control the outgrowth of cells which do not produce proteins of interest in fermentation processes which utilize genetically engineered expression vectors.

BACKGROUND OF THE INVENTION

Fermentation processes have been used for decades in the production of antibiotics and much of this science has proven useful for genetically engineered protein production. Unlike traditional fermentation procedures which involve the culturing of pristine microbes which produce and often secrete the molecule of interest, the genetically altered cells are often unreliable in the maintenance of the expression vector and subsequently in the production of the desired product.

Extrachromosomal elements such as plasmids and other expression vectors are frequently lost when they offer no growth or survival benefit to the host cell. During fermentation processes, host cells which have deleted the extrachromosomal elements no longer suffer the metabolic drain of maintaining these expression vectors and are thus unimpeded in their rate of growth. In a short period of time, host cells which do not contain these extrachromosomal elements will overgrow those host cells whose growth is retarded by expression and accumulation of the product of interest. This process of negative selection toward unadvantageous genetic material has been documented for years in studies of drug-resistant bacteria. It is well established that removal of the antibiotic, towards which resistance is conferred by a plasmid encoded gene, gives rise to a population of bacteria with the drug-resistant plasmid maintained in only a small percentage of the bacteria.

Antibiotic resistance genes are often engineered into expression vectors to allow selection of transformants and transfectants and to provide selective pressure toward retention of the expression system during prolonged culturing. The selective pressure exerted by the antibiotic ensures maintenance of the drug resistant phenotype, but does not preclude the appearance of plasmids which confer antibiotic resistance but lack the capacity to form the product of interest. Production of an extraneous protein is a metabolic drain on the cells expressing and accumulating the polypeptide product of interest and results in a selection pressure towards cells which no longer form the product.

The present invention comprises the addition of an antibiotic or combination of antibiotics at bacteristatic or bactericidal concentrations to the fermentation mixture at approximately the time product expression is induced. The addition of bacteristatic or bactericidal concentrations of an antibiotic at approximately the time of product induction will effect all cells; however, cells producing product are already impeded in cell division capacity and therefore the addition of antibiotic functions to prevent outgrowth of aberrant expression systems.

The use of antibiotics for purposes of this invention has not been previously disclosed. The prior art has revealed that antibiotics are frequently used to eliminate plasmids and other extrachromosomal elements from host cells. Michel-Briand, et.al.,1986, J. Antimicrob. Chemother. 18: 667–674 reported the use of several 4-quinolone derivatives including cinoxacin and novobiocin to eliminate various drug resistant plasmids from members of Enterobacteriacae. Numerous other references including: Trevors, 1986, FEMS Microbiol. Rev. 32: 149–157 ; Wolfson, et.al., 1982, J. Bacteriol., 152: 338–344; and Weissner and Wiedemann, 1987, J. Antimicrob. Chemother., 18: 575–584 similarly teach the use of antibiotics for plasmid curing. The present invention differs significantly from the prior art use of antibiotics for expression vector elimination; indeed, this would be contrary to the purpose of the present invention.

Until the present invention, no method was known for ensuring that the cells in a fermentation process were not overgrown by cells, which having lost the capacity for product expression, were able to grow at accelerated rates.

SUMMARY OF THE INVENTION

The present invention relates to the discovery of a method for preventing the accumulation of aberrant microbes which do not produce the product of interest during fermentations using transformed or transfected prokaryotes. The method of the invention comprises addition of at least a bacteristatic concentration of antibiotic at approximately the time at which expression of the recombinant polypeptide product is induced. Antibiotics with various mechanisms of action have demonstrated utility for purposes of the invention.

For purposes of the present invention as disclosed and claimed herein, the following terms are as described below.

Host Cell—A cell suitable for transformation or transfection with an expression vector.

Expression System—A combination of host cell and expression vector capable of expressing a polypeptide product of interest.

Induction—Fermentation conditions appropriate to cause increased expression of the polypeptide product of interest.

Expression—Transcription and translation of the product of interest.

Fermentation—Aerobic or anaerobic conditions appropriate for the growth of microorganisms.

Bacteristatic—A concentration of an antibiotic which prevents microbial cell division.

Bactericidal—A concentration of an antibiotic which kills actively growing microbial cells.

Aberrant Expression Vector—An expression vector which due to deletion of its regulatory or coding regions no longer expresses the product of interest.

Aberrant Expression System—A host cell containing an aberrant expression vector.

Fidelity—Ability of an expression vector to maintain product expression.

Bovine Growth Hormone Derivative—A polypeptide product having bioactivity similar to bovine growth hormone.

Expression Vector—Any agent capable of autonomous replication or genomic integration, including but not limited to plasmids, comprising a DNA molecule into which one or more transcriptional and translational activating sequence(s), and a gene encoding a polypeptide of interest have been incorporated in such a manner as to allow expression of the gene encoding a polypeptide of interest.

DETAILED DESCRIPTION OF THE INVENTION

Figure 1A:
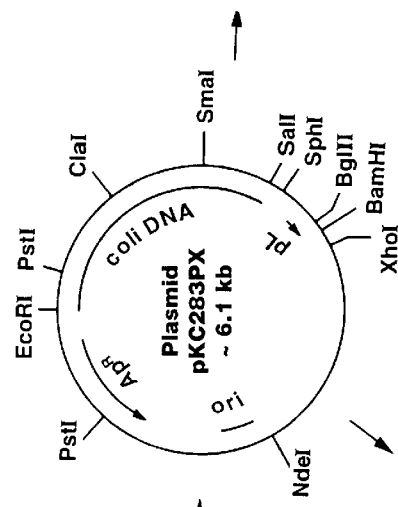
FIG. 1 is a flowchart detailing the construction of plasmid pL32.
Figure 1A:
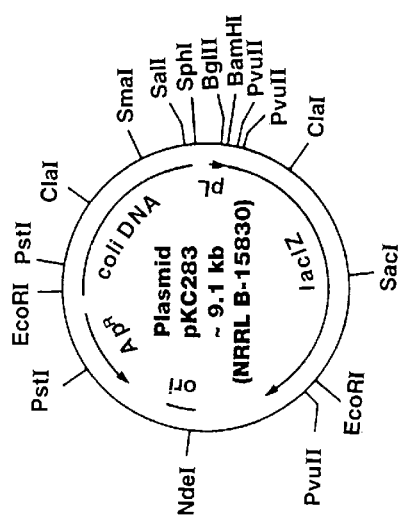
Figure 1B:
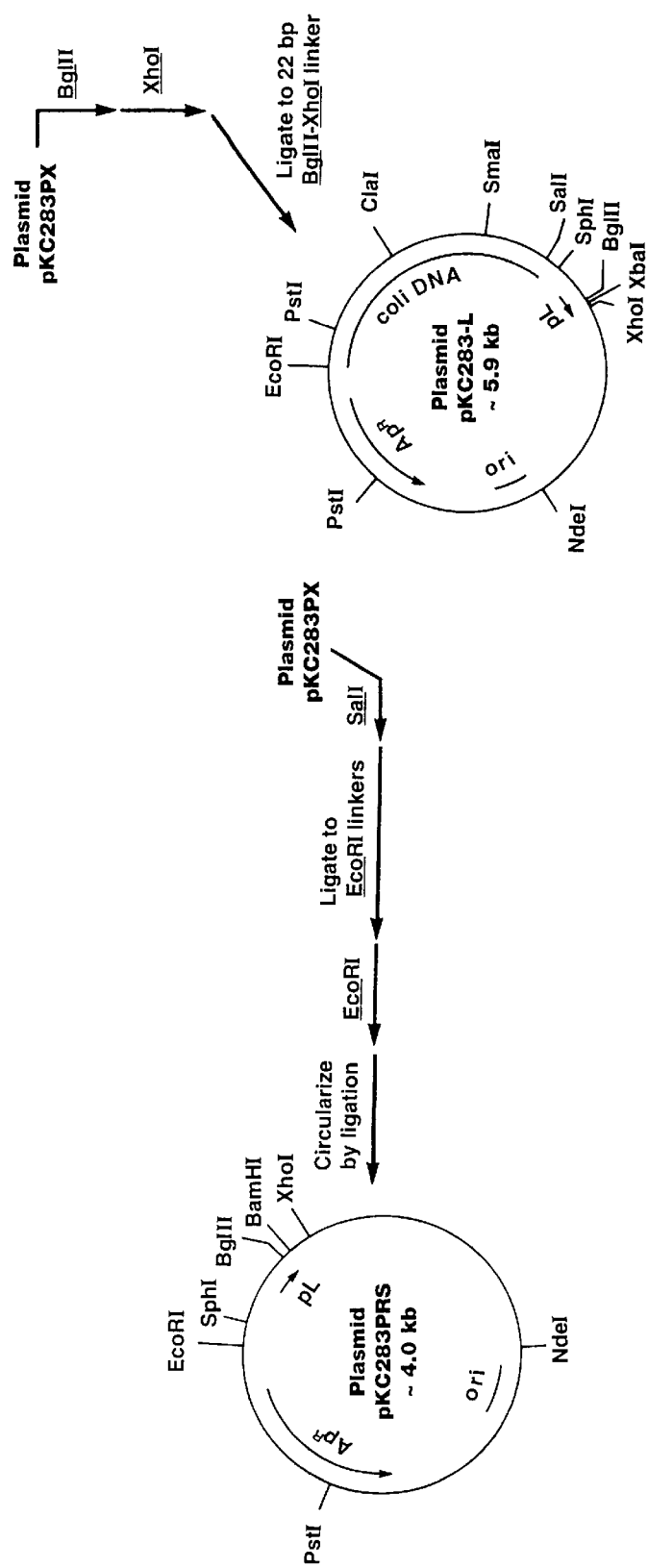
Figure 1C:
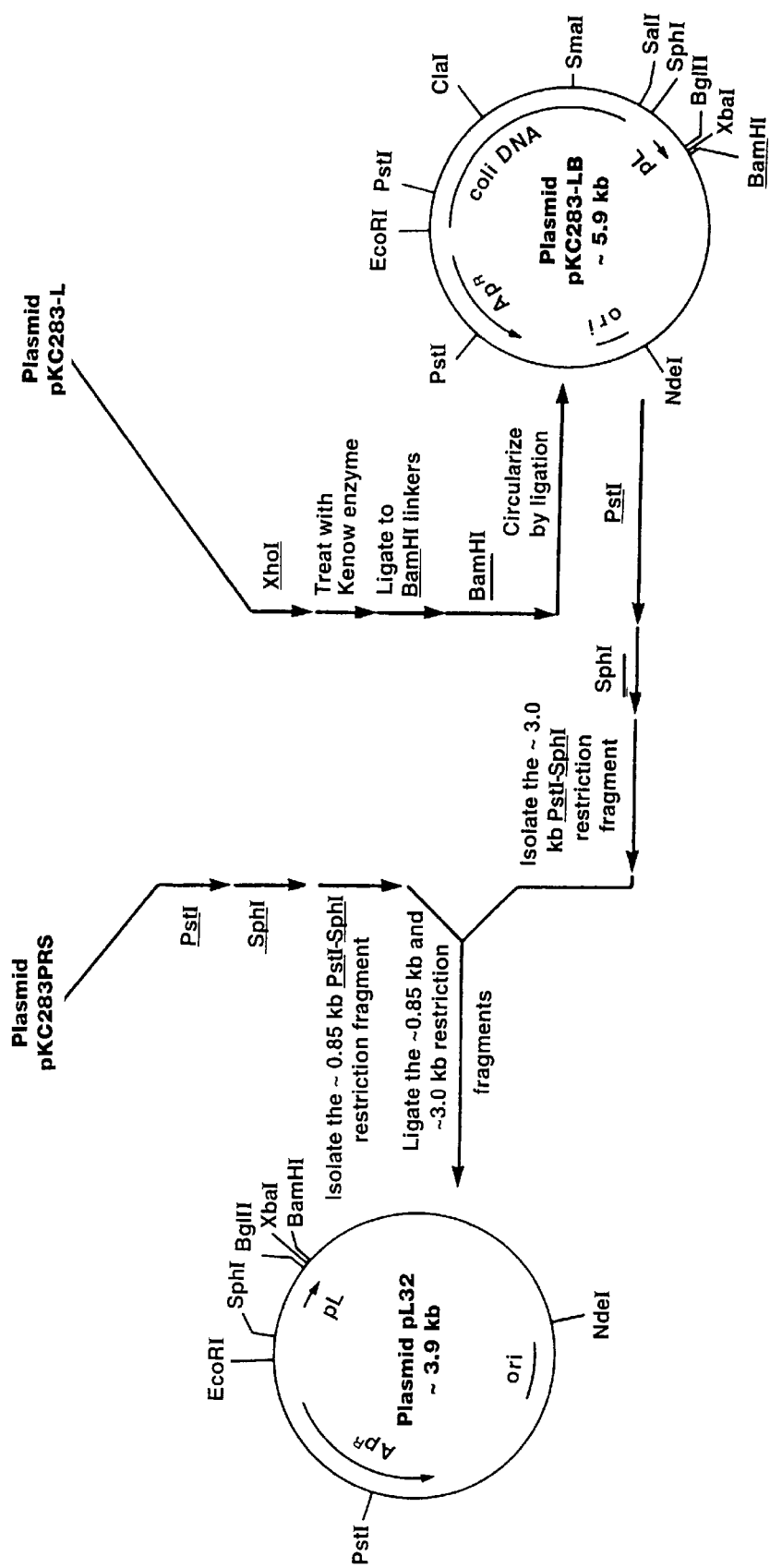

The present invention relates to a method for ensuring expression vector fidelity in fermentation processes utilizing recombinant expression vectors. When expression systems are induced for product expression, a negative selective pressure is exerted upon all cells which produce an extraneous protein. The selective pressure toward a lack of product expression often results in an accumulation of deletant expression vectors. The prior art usage of antibiotics in fermentations does not function to control deletant expression vectors except as related to maintenance of drug-resistant phenotypes.

The present invention comprises the addition of an antibiotic or combination of antibiotics at bacteristatic or bactericidal concentrations to the fermentation mixture at approximately the time product expression is induced. The addition of bacteristatic or bactericidal concentrations of an antibiotic at approximately the time of product induction will effect all cells; however, cells producing product are already impeded in cell division capacity and therefore the addition of an antibiotic functions to prevent outgrowth of aberrant expression systems.

The use of an antibiotic resistance gene on an expression system is known in the art and is desirable, in that the appropriate resistance gene provides a selective pressure towards retention of the expression vector. Examples 1, 2, 3, and 4, while illustrating the present invention also embody the use of an antibiotic resistance selection system which utilizes tetracycline in the fermentation medium and the presence of a tetracycline resistance gene on the expression vector. It is critical to note that the prior art use of antibiotics ensures merely the retention of an antibiotic resistant phenotype.

The expression system used to illustrate the method of the present invention is a thermoinducible expression system providing high level expression of a bovine growth hormone (bGH) derivative. Construction of the expression vector pCZR125 encoding EK-bGH, the bGH derivative used to illustrate the method of the present invention, was constructed from a wide variety of publicly available starting materials.

Plasmid pCZR125 was constructed by first isolating plasmid pKC283 from *E. coli* K12 BE1201/pKC283. This culture may be obtained from the NRRL under accession number NRRL B-15830. Plasmid pKC283 comprises a hybrid lpp-pL promoter of bacteriophage λ. This plasmid is obtained from *E. coli* K12 BE1201 cells because these cells comprise a temperature sensitive cI repressor integrated into the cellular DNA. The unneeded lacZ portion of plasmid pKC283 was excised by first digesting the plasmid with restriction enzyme PvuII. Specific DNA linkers were then added to the digested DNA to convert the PvuII sites into a single XhoI site, which created plasmid pKC283PX.

Detailed descriptions of the isolation of plasmids pKC283 and pKC283PX are presented respectively in Examples 6 and 7. Restriction site and function maps of plasmids pKC283 and pKC283PX are presented in FIG. 1 of the accompanying drawings. As explained in Example 8, plasmid pKC283PX is transformed into *E. coli* K12 MO($\lambda^+$). *E. coli* K12 MO($\lambda^+$) is available from the NRRL under the accession number NRRL B-15993.

Plasmid pKC283PX was next digested with restriction enzymes BglII and XhoI. After the vector was purified, DNA linkers with BglII and XhoI ends were ligated into the vector to form plasmid pKC283-L. The BglII-XhoI linker also contained an XbaI site. The XhoI site of plasmid pKC283-L was next converted into a BamHI site. This was accomplished by a total digestion of plasmid pKC283-L with restriction enzyme XhoI, followed by treatment with Klenow, then addition of BamHI linkers, to form plasmid pKC283-LB. Detailed descriptions of the construction of plasmids pKC283-L and pKC283-LB are presented respectively in Examples 9 and 10. Restriction site and function maps of plasmids pKC283-L and pKC283-LB are presented in FIG. 1 of the accompanying drawings.

The extraneous *E. coli* DNA was next excised from plasmid pKC283PX by total digestion with restriction enzyme SalI, followed by treatment of the ~4.0 kb vector with Klenow, then addition of EcoRI linkers. Upon recircularization via ligation, this formed plasmid pKC283PRS. Plasmid pKC283PRS was then digested with restriction enzymes PstI and SphI and the ~0.85 kb PstI-SphI restriction fragment was isolated. In an analogous manner, plasmid pKC283-LB was digested with restriction enzymes PstI and SphI and the ~3.0 kb fragment was isolated. The ~0.85 kb PstI-SphI fragment of pKC283PRS was then ligated into the ~3.0 kb PstI-SphI vector fragment of pKC283-LB to form plasmid pL32. Detailed descriptions of the construction of plasmids pKC283PRS and pL32 are presented in Example 11. Restriction site and function maps of plasmids pKC283PRS and pL32 are presented in FIG. 1 of the accompanying drawings.

Figure 2:
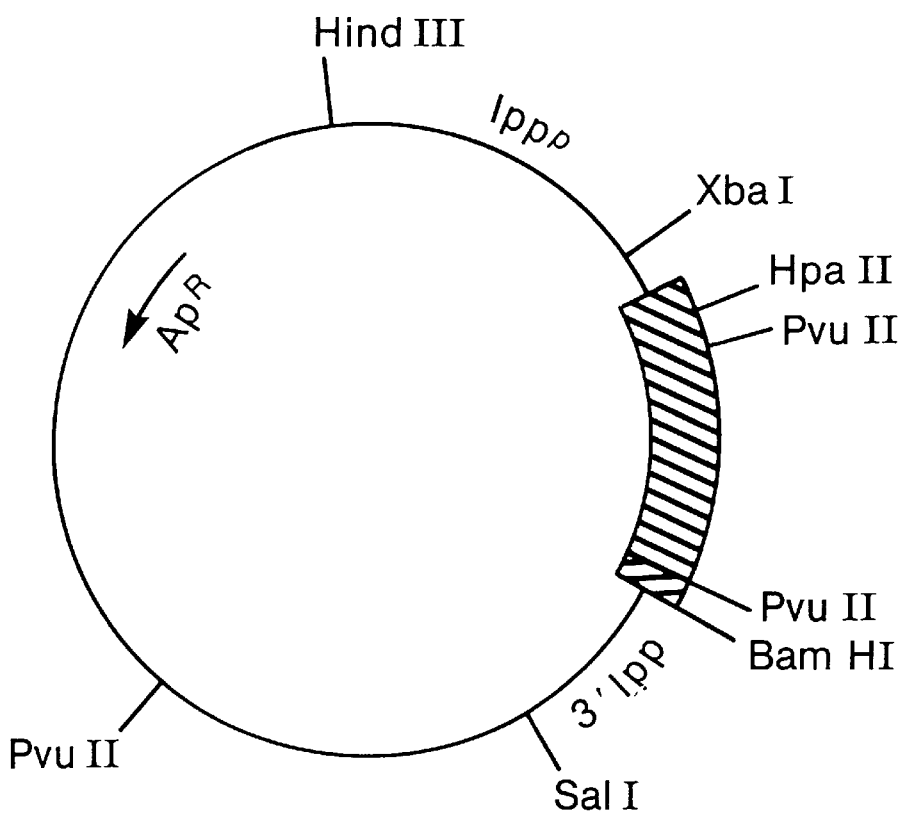
FIG. 2 is a restriction site and function map of plasmid pNM789.
Figure 3:
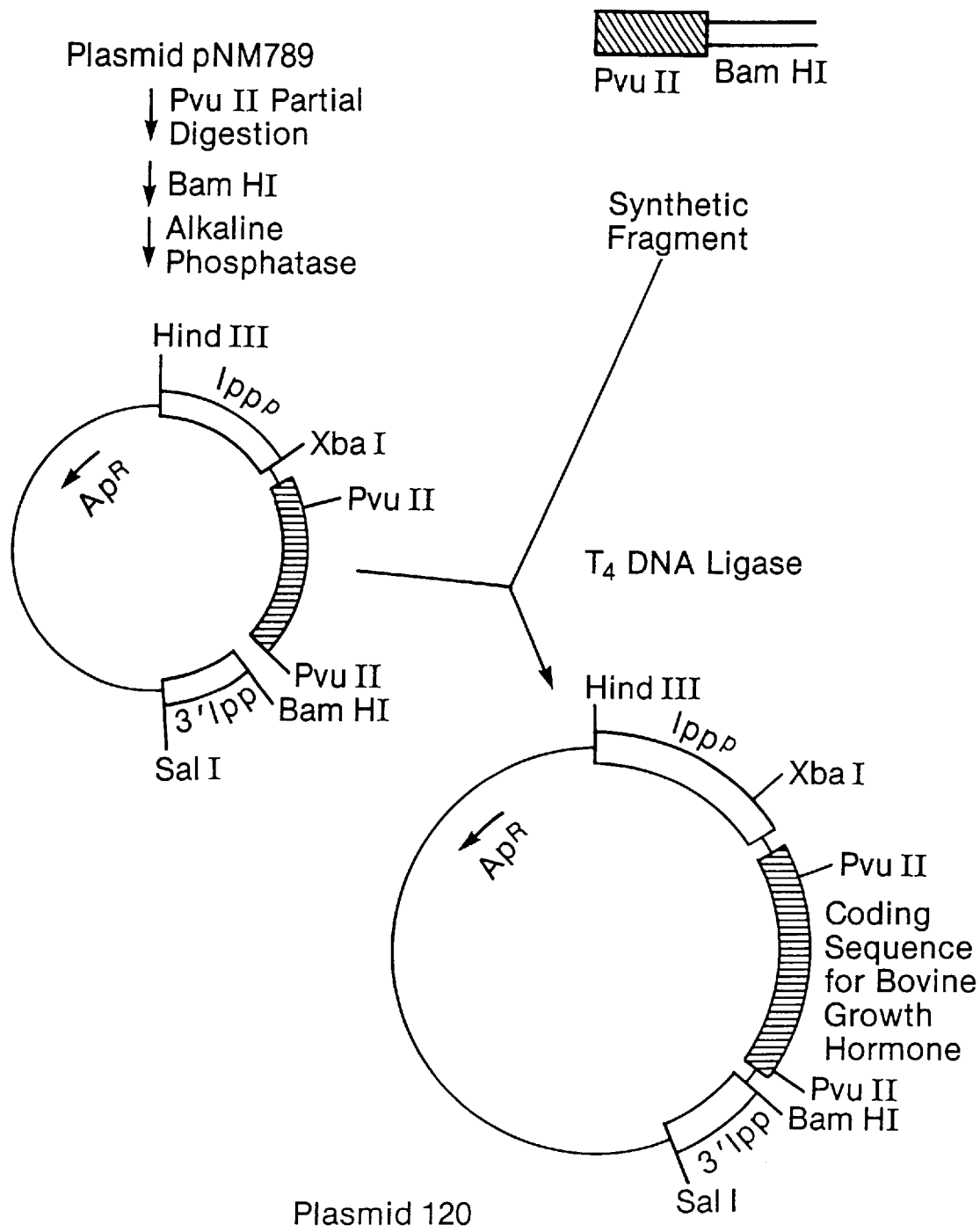
FIG. 3 details the construction of plasmid 120.
Figure 4A:
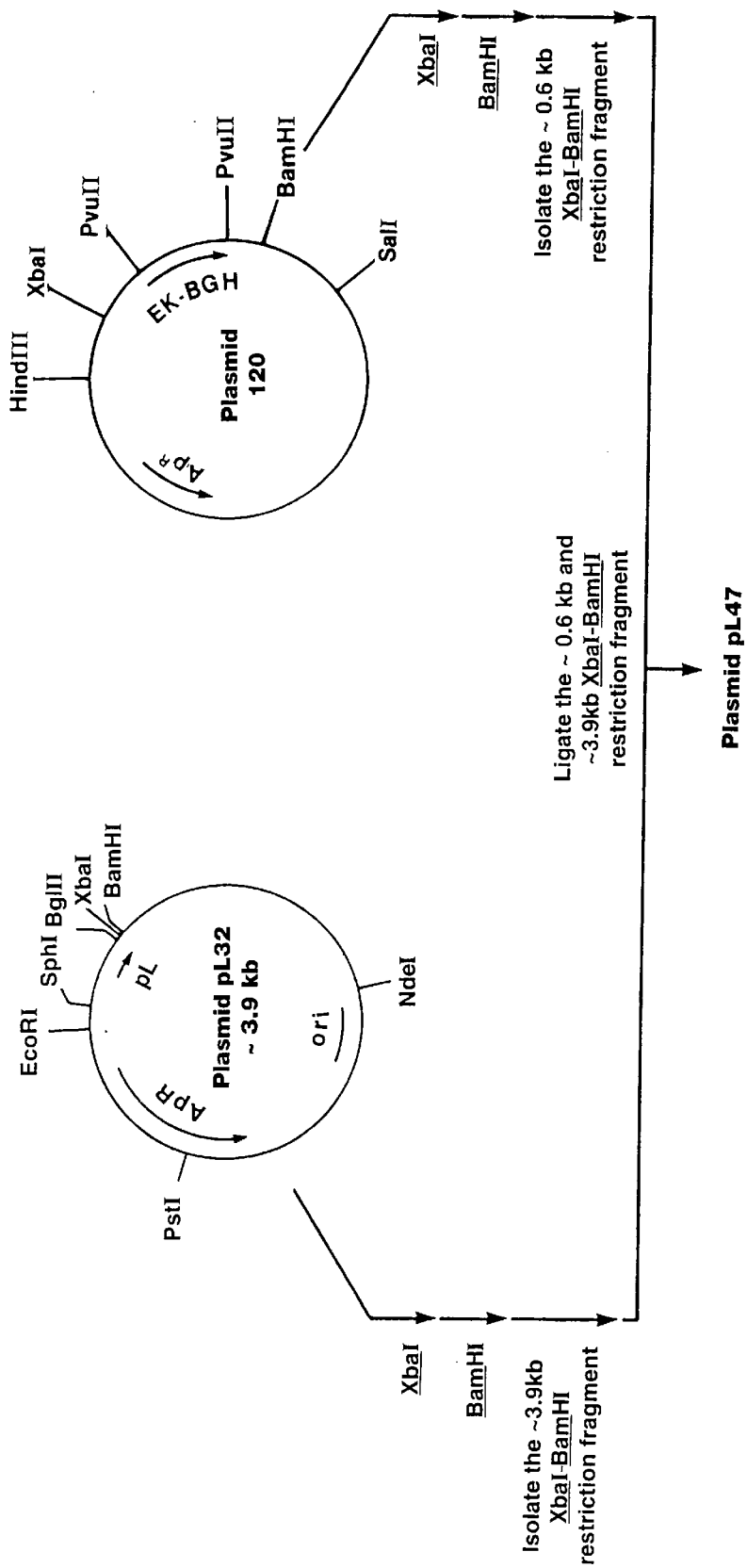
FIG. 4 is a flowchart detailing the construction of plasmid pL110.
Figure 4B:
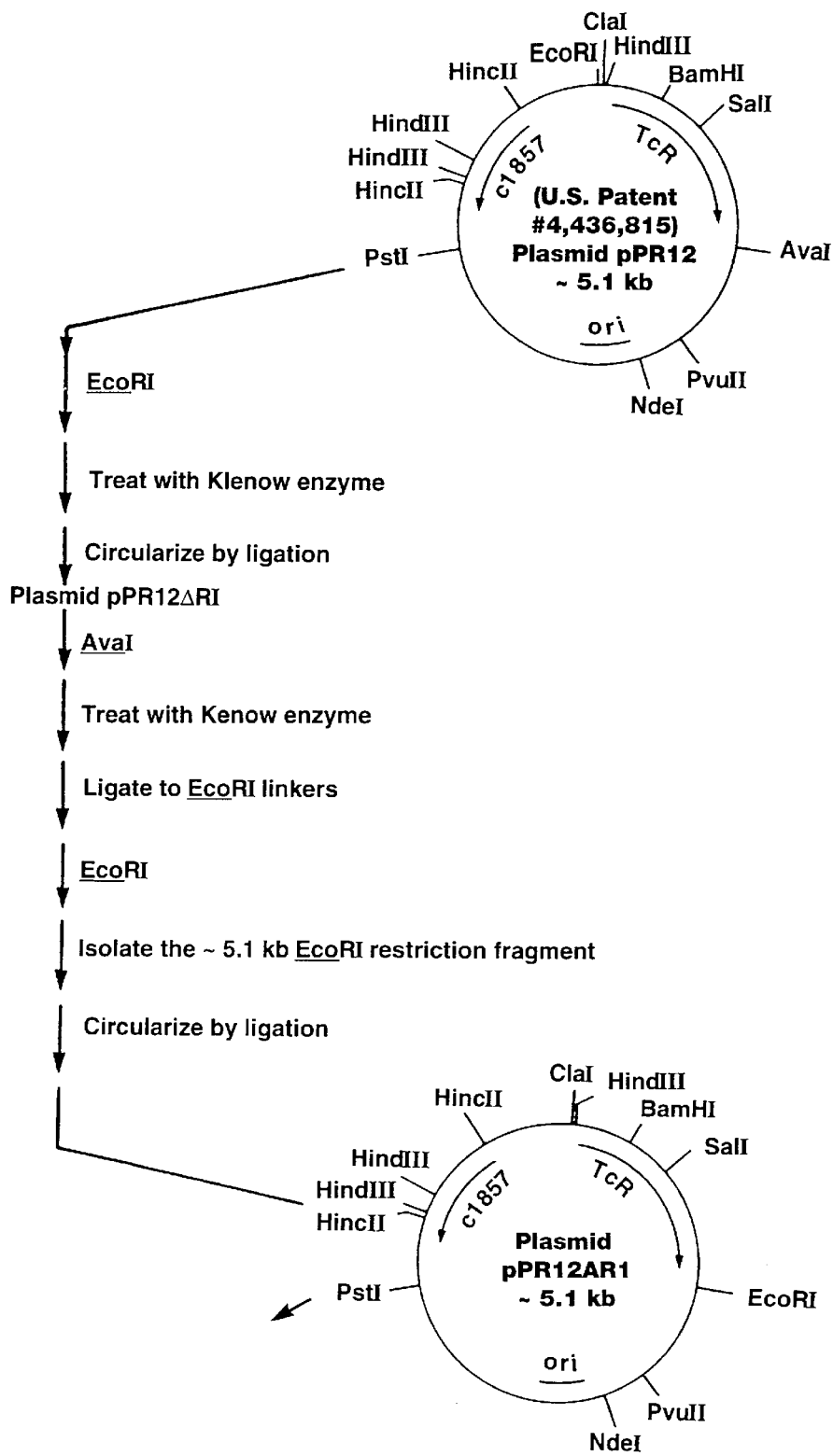
Figure 4C:
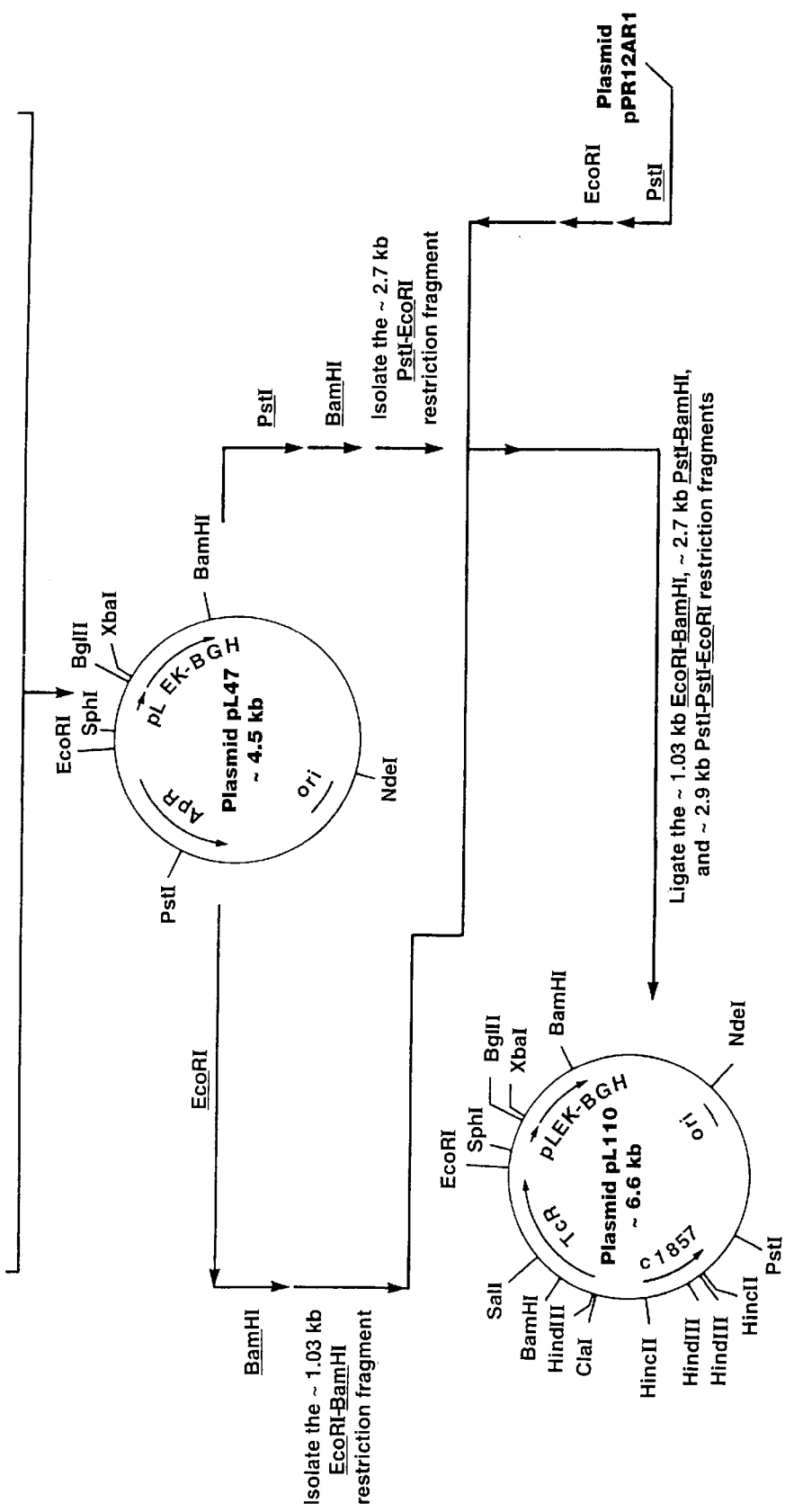

Next, plasmid pNM789 is obtained from the NRRL in *E. coli* K12 RV308/pNM789 under the accession number B-18216. A restriction site and function map of plasmid pNM789 is presented in FIG. 2 of the accompanying drawings. Plasmid pNM789 was partially digested with restriction enzyme PvuII, fully digested with restriction enzyme BamHI, then treated with alkaline phosphatase. Next, a new PvuII-BamHI linker was ligated into the digested, phosphatased vector pNM789 to form plasmid 120. Plasmid 120 was then totally digested with restriction enzymes XbaI and BamHI and the ~0.6 kb XbaI-BamHI EK-bGH-encoding restriction fragment was isolated. Plasmid pL32 was also digested with restriction enzymes XbaI and BamHI and the ~3.9 kb vector fragment was isolated. The ~0.6 kb XbaI-BamHI fragment of plasmid 120 was then ligated into the ~3.9 kb vector fragment of plasmid pL32 to form plasmid pL47. Detailed descriptions of the construction of plasmids 120 and pL47 are presented in Examples 11 and 12. Restriction site and function maps of plasmids 120 and pL47 are presented respectively in FIGS. 3 and 4 of the accompanying drawings.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued 13 Mar., 1984. A restriction site and function map of plasmid pPR12 is presented in FIG. 4 of the accompanying drawings. The EcoRI site was removed from plasmid pPR12 by first totally digesting the plasmid with restriction enzyme EcoRI, followed by treatment with Klenow. The vector was then recircularized by ligation to form plasmid pBR12ΔR1. Plasmid pPR12ΔR1 was then digested with restriction enzyme AvaI and treated with Klenow. The AvaI-digested, Klenow treated pPR12ΔR1 was next ligated to EcoRI linkers, cut with restriction enzyme EcoRI, then recircularized to form plasmid pPR12AR1. A detailed description of the construction of plasmid pPR12AR1 is presented in Example 13. A restriction site and function map of plasmid pPR12AR1 is presented in FIG. 4 of the accompanying drawings.

The ~2.9 kb PstI-EcoRI restriction fragment of plasmid pPR12AR1 was isolated after the plasmid was first digested with restriction enzymes PstI and EcoRI. Plasmid pL47 was digested with restriction enzymes PstI and BamHI and the ~2.7 kb PstI-BamHI restriction fragment was isolated. In a separate reaction, plasmid pL47 was digested with restriction enzymes EcoRI and BamHI and the ~1.03 kb EcoRI-BamHI fragment was isolated. The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to form plasmid pL110. A detailed description of the construction of plasmid pL110 is presented in Example 14. A restriction site and function map of plasmid pL110 is presented in FIG. 4 of the accompanying drawings.

Figure 5:
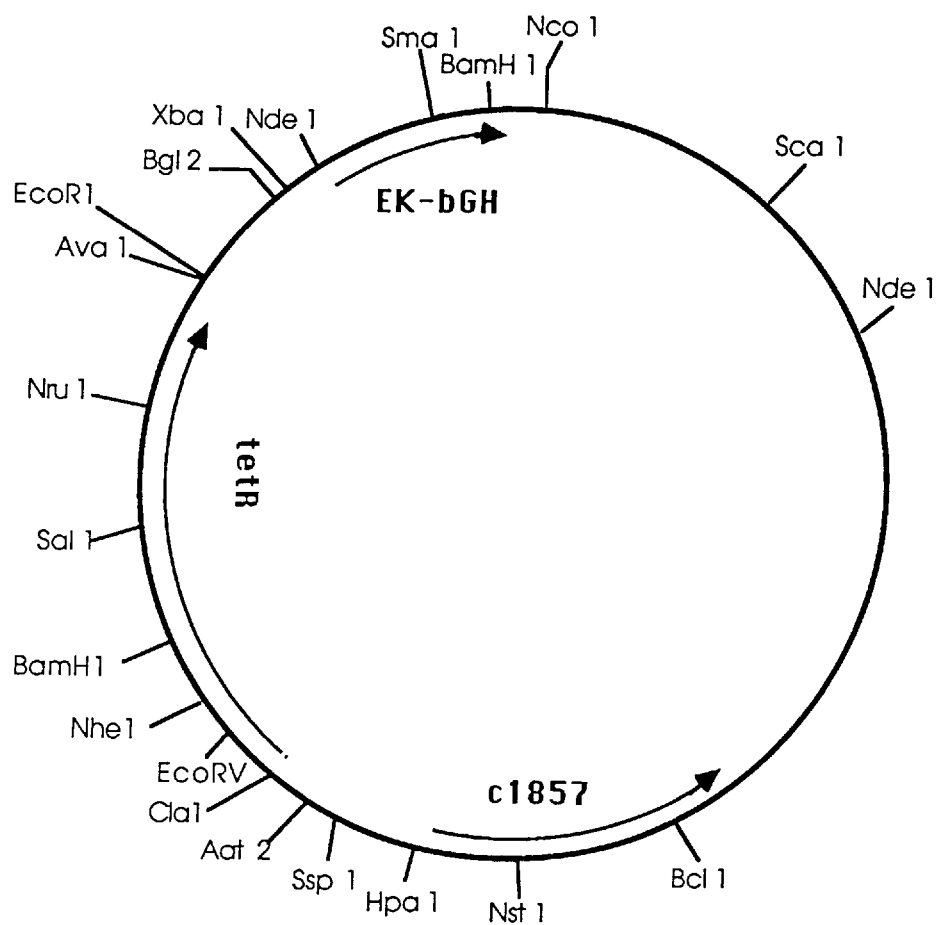
FIG. 5 is a restriction site and function map of plasmid pCZR125.

Plasmid pL110 was digested with the restriction enzymes XbaI and BamHI and the ~5.8 kb fragment was isolated. The 5.8 kb fragment of plasmid pL110 was then ligated to a synthetic DNA sequence, as described in Example 15. The presence of the first cistron promotes higher level expression of met-EK-bGH product. A restriction site and function map of plasmid pCZR125 is presented in FIG. 5 of the accompanying drawings.

*E. coli* RV308 can be obtained from the Northern Regional Research Laboratories in lyophilized form under the accession number NRRL B-15624. *E. coli* RV308 host cells were transformed with plasmid pCZR125 to generate the expression system used throughout this disclosure to exemplify the various embodiments of the present invention.

Figure 6:
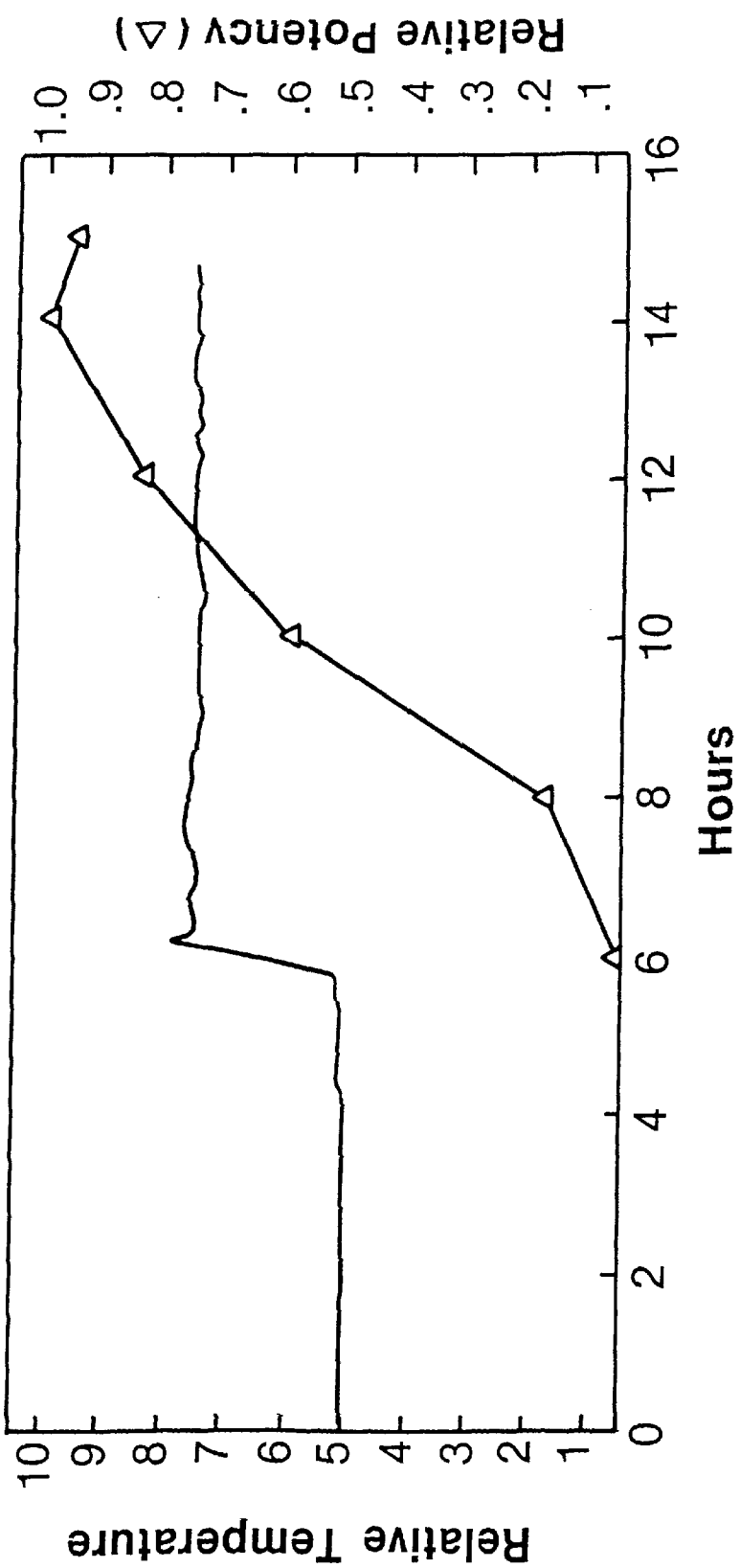
FIG. 6 illustrates the relationship between the induction of product expression and production of EK-bGH. Cinoxacin was added at approximately the six hour time point.

The *E. coli* K12 RV308/pCZR125 expression systems are preferably maintained at temperatures of about 33° C. during the early stages of the fermentation process wherein the expression systems are merely replicating in order to achieve sufficient cell numbers for optimal product expression. When sufficient cell numbers are present, the temperature is raised to induce expression of the EK-bGH. FIG. 6 illustrates the induction of EK-bGH production. The time period of 0 to about six hours represents the time allowed for the expression systems to replicate to sufficient numbers for optimal fermentative production. At about the six hour time point, the temperature is elevated thereby inactivating the temperature sensitive repressor. Upon inactivation of the repressor high level product expression begins.

When thermoinducible expression systems are used, antibiotics added for purposes of the present invention are added at about the time the temperature of the fermentation mixture is increased. Skilled artisans, while realizing the broad applicability of the present invention, will realize that a kinetic analysis of expression vector replication and product expression would be required when expression systems other than those used illustratively herein are used for purposes of the present invention. The present invention teaches that when antibiotics are added at bacteristatic or bactericidal concentrations, at approximately the time at which product expression is induced, the accumulation of aberrant expression systems is prevented.

A thermoinducible expression system was used merely to illustrate the present invention. The present invention is in no way restricted to the use of this type of expression system the details of which were provided merely to promote an understanding of the invention. Any expression system which expresses and subsequently accumulates a recombinant product is at a selective disadvantage in a fermentation process and therefore would benefit from the teachings of the present invention.

Thus, it should be noted that the present invention is not limited to thermoinducible systems. Expression systems in which product expression is driven by inducible promoters such as, for example, the trp, lac, and the tac promoters, are examples of other promoters providing further embodiments of the invention. Induction of product expression using expression vectors utilizing the aforementioned promoters follows the addition of derepressors, substances which negate the effect of repressor proteins. For example, addition of 3-indolylacetic acid to expression systems using the trp promoter results in the derepression of the promoter and subsequent expression of the gene encoding the product of interest. Expression systems using the lac or tac promoters are likewise derepressed upon addition of isopropyl-β-D-thiogalactoside. The use of the present invention in these expression systems would comprise the addition of bacteristatic or bactericidal concentrations of antibiotics at about the time product expression is induced through addition of the appropriate derepressor.

Skilled artisans are aware that temperature sensitive mutants of many repressors are known in the art. Induction of product expression in systems using these temperature sensitive regulatory systems occurs when culture conditions are elevated. Maniatis et al., "Molecular Cloning-A Laboratory Manual", 1982, Cold Spring Harbor, N.Y., reviews various expression systems and discusses mechanisms of their induction. Application of the present invention to any expression system utilizing a prokaryotic host cell transformed or transfected with an expression vector requires only the addition of bacteristatic or bactericidal concentration of an antibiotic at approximately the time when product expression is induced.

The term "approximately the time" includes brief time periods preceding and subsequent to the induction of product expression. Prior to induction of product expression, there exists a time period wherein the expression systems are merely allowed to replicate. The "seeding" of a fermentation process with less than optimal numbers of expression systems is common in the art of fermentation. Thus, for purposes of the present invention, the addition of bacteristatic or bactericidal concentrations of at least one antibiotic occurs when sufficient expression vectors are present and may briefly precede the induction of product expression. Likewise, the addition of bacteristatic or bactericidal concentrations of at least one antibiotic can occur subsequent to product induction. Addition of bacteristatic or bactericidal concentrations of at least one antibiotic is also included in the "approximately the time" term, if the antibiotic is added within a brief period following product induction. The brief period following induction of product expression, during which addition of bacteristatic or bactericidal concentrations of at least one antibiotic can be performed to practice the present invention, precedes the time point in the fermentation process wherein the accumulation of the product of interest within cells expressing the product places them at a disadvantage in terms of cell division and thus encourages the outgrowth of cells which are not expressing the product. Generally, the addition of antibiotic to practice the present invention will be made within about two hours of induction of product expression, and preferably within about one hour of product induction.

DNA synthesis inhibitors such as, for example: nitrofurans, acrosaxacin, novobiocin oxolinic acid, pipemedic acid, piromidic acid, norfloxacin, anthramycin, bleomycin, nitroimadizoles, and especially cinoxacin are most preferred for purposes of the present invention. Other antibiotics which are of use in the present invention include cell wall inhibitors, such as, for example: penicillins, cephalosporins, vancomycin, cycloserine, alafosfolin, clavulanic acid, bacitracin, moenomycin, and ristocetin, and especially ampicillin. Vitamin analogs, such as, for example: sulfonamides and trimethoprim; and enzyme inhibitors such as, for example, clavulanic acid are also suitable for purposes of the invention and therefore are included in the scope thereof. Those skilled in the art will recognize that the aforementioned antibiotics are merely illustrative of antibiotics suitable for purposes of the invention and that substitutions with various other antibiotics is possible without exceeding the scope of the present invention.

The present invention has been practiced in both defined and complex media formulations. Complex media are preferred for use in the present invention. Examples 1 and 3 illustrate the method of the invention in defined and complex media respectively, while Example 2 serves as a control group for the first Example and Example 4 serves as the control for Example 3. Those skilled in the art realize that the medium used in a fermentation process is critical to maximizing product expression. Nutritional requirements vary from expression system to expression system and a variety of media including, for example, those discussed in Maniatis, et al., Molecular Cloning—A Laboratory Manual, 1982, Cold Spring Harbor, N.Y., should be evaluated to determine the best medium for the particular expression system used in practicing the present invention.

Results of the fermentations detailed in Examples 1, 2, 3, and 4 are summarized in Table 1. The data on deletant expression vectors were obtained from restriction endonuclease analysis of expression vectors isolated from the fermentative mixture at the end of fermentation. The use of restriction analysis to characterize expression vectors is well known in the art. The methodology for the generation and the interpretation of restriction endonuclease mapping of expression vectors is well known in the art. Maniatis, Fritsch, and Sambrook in "Molecular Cloning—A Laboratory Manual", 1982, Cold Spring Harbour Laboratory, Cold Spring Harbor, N.Y., provides an excellent review of this subject.

TABLE I

| Example | Medium | Cinoxacin (20 mcg/ml) | Dry Cell Wt. (g/L) | Relative Potency (non-dimensional) | Deletants |
|---|---|---|---|---|---|
| 1. | Defined | Yes | 9.50 | 0.649 | No |
| 2. | Defined | No | 8.38 | 1.019 | Yes |
| 3. | Complex | Yes | 13.52 | 0.904 | No |
| 4. | Complex | No | 9.62 | 1.103 | Yes |

Table I clearly demonstrates that an antibiotic, when used in accordance with the teachings of the present invention, prevents the accumulation of deletant expression vectors during fermentation processes, utilizing either defined or preferably complex medium formulations.

The relative potency values are an index of bovine growth factor activity. Monitoring of bovine growth hormone derivative production was accomplished by a combination of chromatographic and bio-assay procedures.

The concentration of the bGH derivative in the fermentation samples was determined by comparison to reference EK-bGH using standard HPLC techniques. The activity of EK-bGH in the samples was determined using the bio-assay as taught in Example 5. Skilled artisans will appreciate that a bio-assay is essential for initial determinations of any biomolecule. Biochemical and immunochemical assays are useful in determining total amounts of bGH; however bioassays provide information on the amount of functional material. Bioassays are a preferred method of determining bGH activity in samples. When bioassay results are consistently found to be in agreement with HPLC analysis, or for example, radio-immunoassay or enzyme-linked immunosorbent assays it is preferable to rely on these inexpensive and less time consuming analyses. The relative potency estimates reported in Table I and FIG. 6 derive from an HPLC analysis which has been found to correlate well with bio-assay data.

Complex media are preferred for use in the present invention as reference to Table I will illustrate. A modest depression in bovine growth factor production was observed when complex medium was supplemented with cinoxacin at approximately the start of product expression. A substantial depression in EK-bGH production was observed when a defined medium was used. Growth of expression systems in defined medium and supplementing the defined medium to make it a complex medium at approximately the time when antibiotics are added and product expression is induced is also contemplated in the present invention and included in the scope thereof.

The data obtained with cinoxacin merely illustrates the invention and those skilled in the art will realize that any antibiotic which does not disrupt expression of the recombinant polypeptide product of interest would be appropriate for purposes of the invention and therefore is included within the scope thereof.

Cinoxacin is a preferred antibiotic for practicing the present invention. Those skilled in the art will realize that the effective concentration range of antibiotics comprises the bacteristatic or bactericidal range of the particular antibiotic or antibiotics being used. The effective antibiotic concentration range is readily determined by the skilled artisan and will depend on the particular expression systems, the cell density of the expression systems, the particular antibiotic or antibiotics used, as well as the fermentation conditions.

When cinoxacin is used to practice the present invention in fermentations utilizing the *E. coli* RV308/pCZR125 expression system for EK-bGH production, the preferred cinoxacin concentration is in the range of from about 5 ug/ml to about 50 ug/ml with about 10 ug/ml to about 20 ug/ml being especially preferred. The preferred concentrations stated above relate to the fermentative production of EK-bGH in the RV308/pCZR125 expression system and are merely illustrative of the present invention and are not limiting upon the scope thereof.

To further illustrate the method of the invention, fermentations were conducted using ampicillin and novobiocin (both obtained from Sigma Chemical Co., St. Louis, Mo. 63178) in the *E. coli* RV308/pCZR125 EK-bGH fermentation process. Ampicillin was used at a concentration of about 25 mcg/ml, while novobiocin was used at about 50 mcg/ml. Both of the aforementioned antibiotics, when added at approximately the time the product expression was induced, were effective in preventing the accumulation of deletant expression vectors. The concentrations of the antibiotics used are merely illustrative and skilled artisans realize that concentrations of any antibiotic used for purposes of the invention is limited only to those concentrations which comprise the bacteristatic or bactericidal range of said antibiotic.

The numerous antibiotics which are suitable for purposes of the invention, the compatibility of the present invention with a variety of media, and the applicability of the method of the invention to numerous host cell/expression vector systems indicate that the present invention is a significant advance in the technical art of fermentation.

The host cell used for illustrating the present invention was *E. coli* K12 RV308 and this strain is preferred. Skilled artisans realize that other host cells, such as, for example: Other Enterobacteria, Bacillus species, and Streptomycetes species would also be amenable to the method of the present invention.

The Examples disclosed to illustrate the present invention are merely representative of polypeptide products which can be produced using the present invention. A bovine growth hormone derivative is the polypeptide product used in the examples to illustrate the invention, however skilled artisans will recognize that other polypeptide products of interest encoded on expression vectors would be suitable for use in the present invention, such as, for example: β-galactosidase, human pre-proinsulin, human proinsulin, human insulin A-chain, human insulin B-chain, non-human insulin, human growth hormone, insulin like growth factors, bovine growth hormone, human interferon, non-human interferon, viral antigens, urokinase, tissue-type plasminogen activator, interleukins 1–6, colony stimulating factors, erythropoetin, and the like.

The Examples set forth below are intended to assist in a further understanding of the invention. Particular materials employed, species, and conditions, are intended to be further illustrative of the invention and not limiting of the reasonable scope thereof.

EXAMPLE 1

The present invention has been illustrated using cinoxacin, (available from Eli Lilly and Co., Indianapolis, Ind. 46285) to prevent the appearance of detectable levels of deletant plasmids during a fermentative process for production of a bovine growth hormone derivative.

A medium formulation described by Domach, et. al., 1984, Biotechnology and Bioengineering, vol. xxvi: 203–206 was used for purposes of teaching the invention, said medium consisting of: Ammonium Sulfate Technical Grade, 0.125% (VanWaters & Rogers, 7425 E. 30th St. Indianapolis, Ind. 46219;) Potassium Phosphate Monobasic, 0.150% (Ulrich Chemical Inc., 3111 North Post Rd., Indianapolis, Ind. 46226) Sodium Chloride, 0.001% (Central Indiana Supply Co., P.O. Box 762, Indianapolis, Ind. 46206); Potassium Phosphate, Dibasic, 0.3% (Ulrich Chemical Inc., Terre Haute, Ind. 47808) Ferrous Sulfate, 0.1% (Mays Chemical Co., Inc. Indianapolis, Ind. 46226); Sodium EDTA-7H20, 0.00372% (Sigma Chemical Co., St. Louis, Mo. 63178); Magnesium Sulfate for Fermentation, 0.01% (VanWaters & Rogers, Indianapolis, Ind. 46219); Glucose (80%), 0.85%. Thiamine, 0.0005% (SST Corporation, Clifton, N.J. 07012); and Tetracycline 0.0015% (Sigma Chemical Co., St. Louis, Mo. 63178) were added as supplements to the basic medium of Donach et al. for nutritional and selective purposes respectively.

The transformed microbes were cultivated under conditions suitable for growth until numbers sufficient for optimal product expression were obtained. Expression of the recombinant polypeptide product was induced and at approximately the same time sterile filtered cinoxacin was added to achieve a final concentration of 20 mcg/ml. Fermentation continued in the presence of the cinoxacin and expression of the recombinant polypeptide product was monitored by sampling the fermentation mixture and assaying for bovine growth hormone activity. A representative fermentation is illustrated in FIG. 6.

EXAMPLE 2

Another fermentation was performed in substantial accord with the procedure of Example 1. In this procedure, cinoxacin was not added, thereby serving as a control group and allowing the determination as to the extent to which cinoxacin can prevent deletant expression vector accumulation.

EXAMPLE 3

The method of the present invention was further illustrated using a complex medium prepared by addition of 0.5% w/v autolyzed yeast (Difco Laboratories, Inc., Detroit, Mich. 48232) to the medium of Example 1. Cells were cultured under conditions appropriate for growth until sufficient cell numbers were attained. Product expression was induced and at approximately the same time, cinoxacin was added to achieve a final concentration of 20 mcg/ml. Fermentation was allowed to continue in the presence of cinoxacin.

EXAMPLE 4

Another fermentation was performed in substantial accord with the procedure of Example 3. In this procedure, cinoxacin was not added, thereby serving as a control group and allowing the determination as to the extent to which cinoxacin can prevent deletant expression vector accumulation.

EXAMPLE 5

Bioassay of Bovine Growth Hormone Activity

Bovine growth hormone activity was analyzed for biological activity using the following "Tibia Assay".

Female rats, hypophysectomized at 25 days of age, are given, in addition to rat chow, 5% glucose water ad libitum for the first 48 hours following hypophysectomy after which normal tap water is used. On the 7th day (32 days of age) after hypophysectomy animals that are obviously sick or weak are eliminated. All remaining rats are earmarked and weighed. At day 14 (39 days of age) after hypophysectomy the rats are weighed again. Rats that have gained more than 10 grams during the seven-day period and those weighing in excess of 120 grams are eliminated.

The test compound is dissolved in a minimum of 0.01M $NaHCO_3$, pH 8.0 and then is brought to the desired final volume by addition of physiological saline (0.1N NaCl) or distilled water.

On the 14th day after hypophysectomy (39 days of age) the animals are randomized into control and treatment groups. One group serves as control and receives vehicle only. All treatments are administered at a volume of 0.1 ml by subcutaneous injection once daily for 4 days. Individual body weights are recorded at the beginning of the assay. Approximately 18–24 hours following the fourth injection, body weights are again recorded, and the rats are sacrificed by carbon dioxide asphyxiation. The sella turcica of each rat is visually checked for completeness of hypophysectomy. The right tibia of each rat is removed, dissected free from soft tissue, and split in a midsaggittal plane with a scalpel to expose a cross-section of the proximal epiphyseal cartilage plate.

The tibias so removed and split are subjected to the following histological preparation. Bone halves are (1) Fixed in 10% neutral formalin for at least 72 hours.

(2) Washed thoroughly in deionized water for one hour.

(3) Immersed in acetone for one hour.

(4) Washed again in deionized water for one hour.

(5) Immersed in 2% silver nitrate for exactly 2 minutes and then immediately placed in deionized water while being exposed to strong light for 6 minutes (calcified parts appear dark brown).

(6) Rapidly removed from water and submerged immediately and fixed in 10% sodium thiosulfate for about 30 seconds.

(7) Washed thoroughly in deionized water for 30 minutes and maintained in deionized water until reading.

Following reading, the bones are stored in 80% ethanol in the dark.

The width of the uncalcified epiphyseal cartilage is determined. A binocular dissecting scope with a 10× occular lens (reticle micrometer eyepiece with 0.1 mm divisions) and a 4× objective lens is used for determining the cartilage plate width. The separate readings are made across the epiphyseal plate and recorded on the data sheet. Using a scope having the above lens configuration, the width of the epiphyseal plate in micra is calculated by multiplying each value by 25 (with this lens configuration, 1 mm on a ruler is covered by 40 small divisions on the reticle; therefore, one division=25 microns). The arithmetic means of all ten readings for each bone are calculated. The mean of all bones within a treatment group are also calculated.

Using the above method, the results depicted in the Table following were obtained. The bovine growth hormone is compared against the vehicle as Control and a sample of pituitary source standard bovine growth hormone obtained from the National Pituitary Agency (Compound II).

EXAMPLE 6

Isolation of Plasmid pKC283

Lyophils of *E. coli* K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 $\mu$g/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 $\mu$g/ml ampicillin in a manner so as to obtain a single colony isolate of *E. coli* K12 BE1201/pKC283. The single colony obtained was inoculated into 10 ml of LB medium containing 50 $\mu$g/ml ampicillin and incubated overnight at 32° C. with vigorous shaking. The 10 ml overnight culture was inoculated into 500 ml LB medium containing 50 $\mu$g/ml ampicillin and incubated at 32° C. with vigorous shaking until the culture reached stationary phase.

The following procedure is adapted from Maniatis et al., 1982, *Molecular Cloning* (Cold Spring Harbor Laboratory).

The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentraton was about 600 $\mu$g/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 $\mu$g/$\mu$l. A restriction site and function map of plasmid pKC283 is presented in FIG. 1 of the accompanying drawings.

EXAMPLE 7

Construction of Plasmid pKC283PX

About 10 $\mu$l of the plasmid pKC283 DNA prepared in Example 1 were mixed with 20 $\mu$l 10× medium-salt restriction buffer (500 mM NaCl; 100 mM Tris-HCl, pH 7.5; 100 mM MgCl₂; and 10 mM DTT), 20 μl 1 mg/ml BSA, 5 μl restriction enzyme PvuII (~50 Units, as defined by Bethesda Research Laboratories (BRL), from which all restriction enzymes used herein were obtained), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 μl of TE buffer.

About 600 picomoles (pM) of XhoI linkers (5'-CCTCGAGG-3') were kinased in a mixture containing 10 μl 5× Kinase Buffer (300 mM Tris-HCl, pH 7.8; 50 mM MgCl₂; and 25 mM DTT), 5 μl 5 mM ATP, 24 μl H₂O, 0.5 μl of T4 polynucleotide kinase (about 2.5 units as defined by P-L Biochemicals), 5 μl 1 mg/ml BSA, and 5 μl of 10 mM spermidine by incubating the mixture at 37° C. for 30 minutes.

About 12.5 μl of the kinased XhoI linkers were added to the 5 μl of PvuII-digested plasmid pKC283 DNA, and then 2.5 μl of 10× ligase buffer (300 mM Tris-HCl, pH 7.6; 100 mM MgCl₂; and 50 mM DTT), 2.5 μl of 1 mg/ml BSA, 7 μl of 5 mM ATP, 2.5 μl (about 2.5 units as defined by P-L Biochemicals) of T4 DNA ligase, 2.5 μl of 10 mM spermidine, and 3 μl of water were added to the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10.0 mM MgCl₂; and 1 mM DTT). About 10 μl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 1 of the accompanying drawings.

EXAMPLE 8

Construction of *E. coli* K12 MO(λ⁺)/pKC283PX

*E. coli* K12 MO(λ⁺) can be obtained from the Northern Regional Research Laboratories in lyophylized form under the accession number NRRL B-15993. *E. coli* K12 MO(λ⁺) comprises the wild-type lambda pL cI repressor gene, so that transcription from the hybrid pL-lpp promoter of the present invention does not occur in *E. coli* K12 MO(λ⁺) cells. The lyophils are reconstituted, single colonies of MO(λ⁺) are isolated, and a 10 ml overnight culture of the MO(λ⁺)cells is prepared in substantial accordance with the procedure of Example 6, except that the temperature of incubation is 37° C. and no ampicillin is used in the growth media.

Fifty μl of the overnight culture were used to inoculate 5 ml of LB media which also contained 10 mM MgSO₄ and 10 mM MgCl₂. The culture was incubated at 37° C. overnight with vigorous shaking. The following morning, the culture was diluted to 200 ml with LB media containing 10 mM MgSO₄ and 10 mM MgCl₂. The diluted culture was incubated at 37° C. with vigorous shaking until the absorbance at 550 nm (A₅₅₀) was about 0.5, which indicated a cell density of about 1×10⁸ cells/ml. The culture was cooled for ten minutes in an ice-water bath, and the cells were then collected by centrifugation at 4000 g for 10 minutes at 4° C. The cell pellet was resuspended in 100 ml of cold 10 mM MgSO₄ and then immediately re-pelleted by centrifugation. The cell pellet was resuspended in 100 ml of 30 mM CaCl₂ and incubated on ice for 20 minutes.

The cells were again collected by centrifugation and resuspended in 10 ml of 30 mM CaCl₂. A one-half ml aliquot of the cells was added to the ligated DNA prepared in Example 7; the DNA had been made 30 mM in CaCl₂. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred μl aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 6, but the CsCl gradient step was omitted until the desired *E. coli* K12 MO(λ⁺)/pKC283PX transformants were identified. A restriction site and function map of plasmid pKC283PX is presented in FIG. 2 of the accompanying drawings.

EXAMPLE 9

Construction of *E. coli* K12 MO(λ⁺)/pKC283-L

Ten μg of plasmid pKC283PX DNA prepared in accordance with the procedure of Example 6 were dissolved in 20 μl of 10× high-salt buffer, 20 μl 1 mg/ml BSA, 5 μl (~50 units) restriction enzyme BglII, 5 μl (~50 units) restriction enzyme XhoI, and 150 μl of water, and the resulting reaction was incubated at 37° C. for two hours. The reaction was stopped, and after precipitating the BglII-XhoI digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 7. The DNA linker had the following structure:

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, Science 198:1056 and in Crea et al., 1978, Proc. Nat. Acad. Sci. USA 75:5765. In addition, an especially preferred method of synthesizing DNA is disclosed in Hsiung et al., 1983, Nucleic Acid Research 11:3227 and Narang et al., 1980, Methods in Enzymology 68:90.

The linker and BglII-XhoI-digested plasmid pKC283PX were ligated in substantial accordance with the procedure of Example 7. The ligated DNA constituted the desired plasmid pKC283-L. A restriction site and function map of plasmid pKC283-L is presented in FIG. 1 of the accompanying drawings. The plasmid pKC283-L DNA was used to transform E. coli K12 MO($\lambda^+$) and the resulting E. coli K12 MO($\lambda^+$)/pKC283-L transformants were identified in substantial accordance with the procedure of Example 8.

EXAMPLE 10

Construction of E. coli K12 MO($\lambda^+$)/pKC283-LB

About 10 µg of plasmid pKC283-L DNA, prepared in substantial accordance with the procedures of Example 1, were dissolved in 20 µl 10× high-salt buffer, 20 µl 1 mg/ml BSA, 5 µl (~50 units) restriction enzyme XhoI, and 155 µl of H$_2$O, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubation in a dry ice-ethanol bath for five minutes, and centrifugation. The resulting DNA pellet was washed with 70% ethanol, dried, and resuspended in 2 µl 10× nick-translation buffer (0.5M Tris-HCl, pH 7.2; 0.1M MgSO$_4$; and 1 mM DTT), 1 µl of a solution 2 mM in each of the deoxynucleotide triphosphates, 15 µl of H$_2$O, 1 µl (~6 units as defined by P-L Biochemicals) of Klenow, which is the large fragment of E. coli DNA polymerase I, and 1 µl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the procedure of Example 7. After the ligation reaction, the DNA was digested with about 100 units of BamHI for about 2 hours at 37° C. in high-salt buffer. After the BamHI digestion, the DNA was prepared for ligation in substantial accordance with the procedure of Example 2.

The ~5.9 kb BamHI restriction fragment was circularized by ligation and transformed into E. coli K12 MO($\lambda^+$) in substantial accordance with the procedures of Examples 7 and 8. The E. coli K12 MO($\lambda^+$)/pKC283-LB transformants were identified, and then plasmid pKC283-LB DNA was prepared in substantial accordance with the procedure of Example 6. A restriction site and function map of plasmid pKC283-LB is presented in FIG. 1 of the accompanying drawings.

EXAMPLE 11

Construction of E. coli K12 MO($\lambda^+$)/pL32

About 10 µg of plasmid pKC283PX were digested with restriction enzyme SalI in high-salt buffer, treated with Klenow, and ligated to EcoRI linkers (5'-GAGGAATTCCTC-3') in substantial accordance with the procedure of Example 10, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform E. coli K12 MO($\lambda^+$) in substantial accordance with the procedure of Example 8. After the E. coli K12 MO($\lambda^+$)/pKC283PRS transformants were identified, plasmid pKC283PRS DNA was prepared in substantial accordance with the procedure of Example 6. A restriction site and function map of plasmid pKC283PRS is presented in FIG. 2 of the accompanying drawings.

About 10 µg of plasmid pKC283PRS were digested in 200 µl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2–3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 ug of the ~0.85 kb PstI-SphI restriction fragment of plasmid pKC283PRS was obtained in a volume of about 100 µl. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 7. The ligated DNA constituted the desired plasmid pL32. A restriction site and function map of plasmid pL32 is presented in FIG. 1 of the accompanying drawings. Plasmid pL32 was transformed into E. coli K12 MO($\lambda^+$) cells in substantial accordance with the procedure of Example 8. Plasmid pL32 DNA was prepared from the E. coli K12 MO($\lambda^+$)/pL32 transformants in substantial accordance with the procedure of Example 6. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together. Alternatively, plasmid pL32 may be constructed by carrying out the SalI-EcoRI excision and ligation of the first paragraph of this example upon plasmid pKC283-LB.

EXAMPLE 12

Construction of E. coli K12 MO($\lambda^+$)/pL47

E. coli K12 RV308/pNM789 can be obtained from the Northern Regional Research Laboratories in lyophilized form under the accession number NRRL B-18216. A restriction site and function map of pNM789 is presented in FIG. 3 of the accompanying drawings. Plasmid DNA is extracted from the culture in substantial accordance with the teaching of Example 6, except that the temperature of incubation is 37° C. Ten micrograms of pNM789 are suspended in 200 µl PvuII buffer (50 mM Tris-HCl(pH 7.5), 60 mM NaCl and 6 mM MgCl$_2$). One unit of PvuII is added and the reaction mix is incubated for 5 minutes at 37° C. The enzyme is inactivated by heating 10 minutes at 65° C. 30 μl of 10× BamHI buffer (200 mM Tris-HCl (pH 8.0), 1M NaCl and 70 mM MgCl$_2$), 70 μl H$_2$O and 10 units of BamHI are next added and the reaction is incubated for 1 hour at 37° C. This is followed by the addition of 5 units of alkaline phosphatase and incubation for 1 hour at 65° C. The DNA fragments are separated on a 1 percent agarose gel, and a DNA fragment (FIG. 4) the size of a single cut fragment is purified.

A DNA linker with a blunt end and a BamHI end is synthesized in substantial accordance with the teaching of Example 9. This linker (shown in FIG. 4) has the following structure:

The linker is kinased and ligated into the BamHI-PvuII digested plasmid pNM789 in substantial accordance with the teaching of Example 9. This ligation mixture is used to transform E. coli K12 RV308 cells and plasmid isolation is performed upon these transformants in substantial accordance with the teaching of Example 8. Several plasmids are selected which contain the appropriate size PvuII fragment (494 bp) and XbaI-BamHI fragment (628 bp). The sequence of at least two of these is determined by sequencing from the BamHI site toward the unique SmaI site and one clone is selected with the desired sequence. This intermediate plasmid is designated plasmid 120. A schematic outline of this procedure and a restriction site and function map of plasmid 120 is presented in FIG. 4 of the accompanying drawings.

To isolate the EK-bGH-encoding DNA, about 10 μg of plasmid 120 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-bGH was isolated and prepared for ligation in substantial accordance with the procedure of Example 11.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid 120 in substantial accordance with the procedure of Example 7 to yield plasmid pL47. A restriction site and function map of plasmid pL47 is presented in FIG. 5 of the accompanying drawings. Plasmid pL47 was transformed into E. coli K12 MO(λ$^+$) in substantial accordance with the procedure of Example 8, and the E. coli K12 MO(λ$^+$)/pL47 transformants were identified. Plasmid pL47 DNA was prepared from the transformants in substantial accordance with the procedures of Example 6.

EXAMPLE 13

Construction of E. coli K12 RV308/pPR12AR1

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. #4,436,815, issued 13 Mar. 1984. A restriction site and function map of plasmid pPR12 is presented in FIG. 5 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and treated with Klenow in substantial accordance with the procedure of Example 10. After the Klenow reaction, the EcoRI-digested, Klenow-treated plasmid pPR12 DNA was recircularized by ligation in substantial accordance with the procedure of Example 7. The ligated DNA, which constituted the desired plasmid pPR12ΔR1, was used to transform E. coli K12 RV308 in substantial accordance with the procedure of Example 8, except that selection was based on tetracycline (5 ug/ml) resistance, not ampicillin resistance. E. coli K12 RV308 is available from the NRRL under the accession number NRRL B-15624. After the E. coli K12 RV308/pPR12ΔR1 transformants were identified, plasmid pPR12ΔR1 DNA was prepared from the transformants in substantial accordance with the procedure of Example 6.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 10. After the Klenow reaction, the AvaI-digested, Klenow-treated plasmid pPR12ΔR1 DNA was ligated to EcoRl linkers (5'-GAGGAATTCCTC-3') in substantial accordance with the procedure of Example 7. After the linker ligation, the DNA was precipitated and then resuspended in about 200 μl of high-salt buffer containing about 50 units of restriction enzyme EcoRl. The resulting reaction was incubated at 37° C. for about 2 hours. After the EcoRl digestion, the reaction mixture was loaded onto an agarose gel, and the ~5.1 kb EcoRl restriction fragment was purified in substantial accordance with the procedure of Example 11. The ~5.1 kb EcoRl restriction fragment was recircularized by ligation in substantial accordance with the procedure of Example 2. The ligated DNA constituted the desired plasmid pPR12AR1. The plasmid pPR12AR1 DNA was transformed into E. coli K12 RV308 in substantial accordance with the procedure of Example 8, except that selection was based on tetracycline resistance, not ampicillin resistance. After identifying the E. coli K12 RV308/pPR12AR1 transformants, plasmid pPR12AR1 DNA was prepared in substantial accordance with the procedure of Example 6. A restriction site and function map of plasmid pPR12AR1 is presented in FIG. 5 of the accompanying drawings.

EXAMPLE 14

Construction of E. coli K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoRl restriction fragment of plasmid pPR12AR1 was isolated and prepared for ligation in substantial accordance with the procedure of Example 11.

About 10 ug of plasmid pL47 were digested with restriction enzymes PstI and BamHI in 200 ul of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 11. In a separate reaction, about 10 ug of plasmid pL47 DNA were digested with restriction enzymes EcoRI and BamHI in 200 ul of high-salt buffer at 37° C. for two hours, and the ~1.03 kb EcoRI-BamHI restriction fragment that comprised the novel transcriptional and translational activating sequence and the EK-bGH-encoding DNA was isolated and prepared for ligation in substantial accordance with the procedure of Example 11. The ~2 ug of the ~1.03 kb EcoRI-BamHI restriction fragment obtained were used in the construction of plasmid pL110.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 7 and 3, except that tetracycline resistance, not ampicillin resistance, was used as the basis for selecting transformants.

Two PstI restriction enzyme recognition sites are present in the EK-bGH coding region that are not depicted in the restriction site and function maps presented in the accompanying drawings. A restriction site and function map of plasmid pL110 is presented in FIG. 5 of the accompanying drawings.

proceeded at 37° C. for 1 hour. XbaI digested pL110 was then extracted in phenol, a 1/10 volume 3M CH₃COO—Na was added, 3 volumes of ethanol were added; the mixture was incubated in a dry ice-ethanol bath for 5 minutes, and then centrifuged. The precipitated DNA was resuspended in 50 ul H₂O.

The XbaI digested plasmid pL110 was digested with BamHI as follows. 0.2 ul of BamHI (10 U/ul), 10 ul of BamHI buffer (100 mM Tris-HCl, 50 mM MgCl₂, 1M NaCl, and 10 mM 2-Mercaptoethanol, pH 8.0 [at 37° C.], and 90 ul of H₂O was added to the 50 ul of XbaI digested pL110 obtained hereinabove. The digest proceeded for 5 minutes at 37° C. The digested pL110 was extracted in phenol, a 1/10 volumes of CH₃COONa+ was added, followed by addition of 3 volumes of ethanol. Precipitated DNA was resuspended in 50 ul of 10 mM Tris, 1 mM EDTA, pH 8.0 buffer.

The XbaI and BamHI digested pL110 was then loaded onto an agarose gel and the DNA band at about 5.8 kb was isolated. Plasmid pCZR125 was produced by ligating the ~5.8 kb fragment of pL110 to an XbaI to NdeI linker and a synthetic gene encoding EK-bovine growth hormone, which contains an NdeI site on its 5' end and a BamHI site on its 3' end. The XbaI to NdeI sequence was produced using standard oligonucleotide sequence methodology and consists of the following sequence:

EXAMPLE 15

Construction of Plasmid pCZR125

About 26 ug of plasmid pL110 was digested with XbaI as follows. 10× XbaI buffer consists of 600 mM Tris-HCl, 100 mM MgCl₂, 1M NaCl, and 10 mM 2-mercaptoethanol, pH 7.5 (at 37° C.). 50 ul of 10× XbaI buffer, 15 ul of Xba I (10 U/ul), and 185 ul of H₂O were added to the 250 ul of water containing about 25 ug of plasmid pL110. The digestion The above sequence was constructed by chemical synthesis of both strand, followed by mixing to allow hybridization. The gene encoding EK bGH was constructed from 16 chemically synthesized pieces of single-stranded DNA, ranging from 71 to 83 nucleotides long, which together comprise both complementary strands of the entire gene. The synthesis was done by Battelle using an Applied Biosystems (ABS) machine and consists of the following sequence:

-continued
```
TGGGCCCCTGCAGTTCCTCAGCAGAGTCTTCACCAACAGCTTGGTGTTTGGCACCTCGGA
||||||||||||||||||||||||||||||||||||||||||||||||||||||||||||
ACCCGGGGACGTCAAGGAGTCGTCTCAGAAGTGGTTGTCGAACCACAAACCGTGGAGCCT CCGTGTCTATGAGAAGCTGAAGGACCTGGAGGAAGGCATCCTGGCCCTGATGCGGGAGCT
||||||||||||||||||||||||||||||||||||||||||||||||||||||||||||
GGCACAGATACTCTTCGACTTCCTGGACCTCCTTCCGTAGGACCGGGACTACGCCCTCGA GGAAGATGGCACCCCCCGGGCTGGGCAGATCCTCAAGCAGACCTATGACAAATTTGACAC
||||||||||||||||||||||||||||||||||||||||||||||||||||||||||||
CCTTCTACCGTGGGGGGCCCGACCCGTCTAGGAGTTCGTCTGGATACTGTTTAAACTGTG AAACATGCGCAGTGACGACGCGCTGCTCAAGAACTACGGTCTGCTCTCCTGCTTCCGGAA
||||||||||||||||||||||||||||||||||||||||||||||||||||||||||||
TTTGTACGCGTCACTGCTGCGCGACGAGTTCTTGATGCCAGACGAGAGGACGAAGGCCTT GGACCTGCATAAGACGGAGACGTACCTGAGGGTCATGAAGTGCCGCCGCTTCGGGGAGGC
||||||||||||||||||||||||||||||||||||||||||||||||||||||||||||
CCTGGACGTATTCTGCCTCTGCATGGACTCCCAGTACTTCACGGCGCCGAAGCCCCTCCG

CAGCTGTGCCTTCTAG 3'
||||||||||||||||
GTCGACACGGAAGATCCTAG 5'
```

Construction of plasmid pCZR125 was accomplished by ligation of the following site components ~0.28 ug of the 5.8 kb fragment obtained from plasmid pL110 after complete digestion with XbaI and partial digestion with BamHI in a total volume of 2 ul, ~0.18 ug of the synthetic gene encoding a bovine growth factor derivative which has a 5' termini corresponding to a XbaI site and a 3' termini corresponding to a BamHI site in a total volume of 2.5 ul, 8.75 picomoles of the chemically synthesized XbaI to NdeI linker in 1 ul. The plasmid components were added to 6 ul of 5× ligation buffer: 250 mM Tris-HCl, 50 mM MgCl$_2$, 5 mM ATP, 5 mM DTT, 25% v/v polyethylene glycol 8,000, pH 7.6, 2 ul of ligase, and 16.5 ul of H$_2$O. The ligation mixture was incubated overnight at 16° C. The circularized plasmid pCZR125 was then used to transform *E. coli* RV308 cells in substantial accord with the method of Example 8.

I claim:

1. A method of controlling outgrowth of cells having an aberrant expression vector during fermentative production of an expression product, comprising adding at least a bacteriostatic concentration of an antibiotic to a fermentation mixture at approximately the time at which product expression is induced.

2. The method of claim 1, wherein said concentration of antibiotic is a bacteristatic concentration.

3. The method of claim 2 in which said antibiotic is a DNA synthesis inhibitor.

4. The method of claim 3, wherein said DNA synthesis inhibitor is selected from the group consisting of a nitrofuran, cinoxacin, acrosaxacin, novobiocin, oxolinic acid, pipemidic acid, piromidic acid, norfloxacin, anthramycin, and bleomycin.

5. The method of claim 4, wherein said DNA synthesis inhibitor is cinoxacin.

6. The method of claim 4, wherein said DNA synthesis inhibitor is novobiocin.

7. The method of claim 2 in which said antibiotic is a cell wall synthesis inhibitor.

8. The method of claim 7, wherein said cell wall synthesis inhibitor is selected from the group consisting of penicillins, cephalosporins, vancomycin, cycloserine, alafosfolin, fosfomycin, clavulanic acid, bacitracin, moenomycin, and ristocetin.

9. The method of claim 8, wherein said cell wall synthesis inhibitor is ampicillin.

10. The method of claim 2 in which said antibiotic is an enzyme inhibitor.

11. The method of claim 10, wherein said enzyme inhibitor is clavulanic acid.

12. The method of claim 2 in which said antibiotic is a vitamin analog.

13. The method of claim 12, wherein said vitamin analog is selected from the group consisting of a sulfonamide or trimethoprim.

14. The method of claim 1 wherein said concentration of antibiotic is a bactericidal concentration.

15. The method of claim 14 in which said antibiotic is a DNA synthesis inhibitor.

16. The method of claim 15, wherein said DNA synthesis inhibitor is selected from the group consisting of a nitrofuran, cinoxacin, acrosaxacin, novobiocin, oxolinic acid, pipemidic acid, piromidic acid, norfloxacin, anthramycin, and bleomycin.

17. The method of claim 16, wherein said DNA synthesis inhibitor is cinoxacin.

18. The method of claim 16, wherein said DNA synthesis inhibitor is novobiocin.

19. The method of claim 14 in which said antibiotic is a cell wall synthesis inhibitor.

20. The method of claim 19, wherein said cell wall synthesis inhibitor is selected from the group consisting of a penicillin, cephalosporin, vancomycin, cycloserine, alafosfolin, fosfomycin, clavulanic acid, bacitracin, moenomycin, or ristocetin.

21. The method of claim 20, wherein said cell wall synthesis inhibitor is ampicillin.

22. The method of claim 14 in which said antibiotic is an enzyme inhibitor.

23. The method of claim 22, wherein said enzyme inhibitor is clavulanic acid.

24. The method of claim 14 in which said antibiotic is a vitamin analog.

25. The method of claim 24, wherein said vitamin analog is selected from the group consisting of a sulfonamide or trimethoprim.

* * * * *